(12) United States Patent
Wasserscheid et al.

(10) Patent No.: US 7,863,458 B2
(45) Date of Patent: Jan. 4, 2011

(54) HALOGEN-FREE IONIC LIQUIDS

(75) Inventors: Peter Wasserscheid, Erlangen (DE); Andreas Bösmann, Stegen (DE); Roy Van Hal, Köln (DE)

(73) Assignee: Merck Patent GmbH, Darmstadt (DE)

( * ) Notice: Subject to any disclaimer, the term of this patent is extended or adjusted under 35 U.S.C. 154(b) by 1112 days.

(21) Appl. No.: 10/930,674

(22) Filed: Aug. 31, 2004

(65) Prior Publication Data

US 2005/0070717 A1 Mar. 31, 2005

Related U.S. Application Data

(63) Continuation-in-part of application No. PCT/EP03/02127, filed on Feb. 28, 2003.

(30) Foreign Application Priority Data

Mar. 1, 2002 (DE) ................................ 102 08 822

(51) Int. Cl.
C07D 233/56 (2006.01)
B01F 1/00 (2006.01)
C23G 5/00 (2006.01)

(52) U.S. Cl. ................... 548/335.1; 252/364

(58) Field of Classification Search ............... 548/335.1; 252/364

See application file for complete search history.

(56) References Cited

U.S. PATENT DOCUMENTS

| | | | |
|---|---|---|---|
| 5,621,055 A * | 4/1997 | Miyanaga et al. | 526/225 |
| 6,224,877 B1 * | 5/2001 | Gaikar et al. | 424/756 |
| 6,991,718 B2 * | 1/2006 | Moulton | 205/413 |

FOREIGN PATENT DOCUMENTS

| | | |
|---|---|---|
| EP | 0 776 880 A1 | 6/1997 |
| EP | 1 182 196 A1 | 2/2002 |
| EP | 1 182 197 A1 | 2/2002 |
| EP | 1182196 A1 * | 2/2002 |
| JP | 03-182546 | 8/1991 |
| JP | 06-33006 | 2/1994 |
| JP | 08-119878 | 5/1996 |
| WO | WO 01/81329 A1 | 11/2001 |

OTHER PUBLICATIONS

Bossmann et al. (Chem. Comm., 2001, p. 2494-2495).*
Huddleston et al. (Green Chemistry, 2001, v. 3, p. 156-164).*
Carmichael et al. (Proceedings—Electrochemical Society 2000, 99-41, 209).*
Olivier-Bourbigou et al. (Journal of Molecular Catalysis A: Chemical, 2002, v. 182-183, p. 419-437).*
Stock et al. (Green Chemistry (2004), 6(6), 286-290; published on the web May 4, 2004).*
Itoh et al. (Chem. Lett., v. 32, p. 654-55 (2003), published on the web Jun. 27, 2003).*
International Preliminary Examination Report for PCT/EP2003/002127; International Filing Date Feb. 28, 2003.
Welton, Thomas, Room-Temperature Ionic Liquids. Solvents for Synthesis and Catalysis, Chem. Rev. 1999, 2071-2083.
Huddleston, J.G. et al., Room Temperature Ionic Liquids as Novel Media for "Clean" Liquid-Liquid Extraction, Chem. Commun., 1998, 1765-1766.
McGraw-Hill Dictionary of Scientific and Technical Terms, 3rd Edition, 1984, p. 52.
Wikipedia, definition of alkyl, http://en.wikipedia.org/wiki/Alkyl, Apr. 14, 2008.

* cited by examiner

*Primary Examiner*—Robert Havlin
(74) *Attorney, Agent, or Firm*—Rick Matos; Innovar, L.L.C.

(57) ABSTRACT

An ionic liquid according to the invention is substantially halogen-free, has a low viscosity and is stable to hydrolytic degradation under test conditions. The ionic liquid is a compound of the formula (cation) (R'—O—$SO_3$), (cation) (R'—$SO_3$), or a mixture of the two compounds. It can be used in processes for the chemical conversion and separation of materials by employing the ionic liquid as a solvent, solvent additive, extraction agent or phase-transfer catalyst. It can also be used in a heat exchange device wherein the ionic liquid serves as a heat carrier or heat carrier additive.

17 Claims, No Drawings

United States Patent US 7,863,458 B2

HALOGEN-FREE IONIC LIQUIDS

CROSS REFERENCE TO EARLIER FILED APPLICATIONS

The present application is a CONTINUATION-IN-PART of PCT International Application Serial No. PCT/EP03/02127 filed Feb. 28, 2003 and published as PCT International Publication No. WO 03/074494 on Sep. 12, 2003, which claims the benefit of priority of German Patent Application Serial No. DE 102 08 822.5 filed Mar. 1, 2002, the entire disclosures of which are hereby incorporated by reference.

FIELD OF THE INVENTION

The present invention relates to ionic liquids comprising a compound with the general formula (cation) (R'—O—SO$_3$), (cation) (R'—SO$_3$), or a mixture of the two compounds. The invention further relates to processes for the chemical conversion and separation of materials by employing the ionic liquids as solvents, solvent additives, extraction agents or phase-transfer catalysts, and to a device for heat exchange that employs the ionic liquids as heat carriers or heat carrier additive.

BACKGROUND OF THE INVENTION

The term "ionic liquids" is generally understood to mean salts or mixtures of salts whose melting point is below 100° C. (P. Wasserscheid, W. Keim, *Angew. Chem.* (2001), 112, 3926). Salts of this type known from the literature consist of anions, such as halostannates, haloaluminates, hexafluorophosphates or tetrafluoroborates combined with substituted ammonium, phosphonium, pyridinium or imidazolium cations. Several publications have already described the use of ionic liquids as solvents for chemical reactions (T. Welton, *Chem. Rev.* (1999), 99, 2071, P. Wasserscheid, W. Keim, *Angew. Chem.*, (2000), 112, 3926). For example, hydrogenation reactions of olefins with rhodium(I) (P. A. Z. Suarez, J. E. L. Dullius, S. Einloft, R. F. de Souza and J. Dupont, *Polyhedron* 15/7, 1996, 1217-1219), ruthenium(II) and cobalt(II) complexes (P. A. Z. Suarez, J. E. L. Dullius, S. Einloft, R. F. de Souza and J. Dupont, *Inorganica Chimica Acta* 255, 1997, 207-209) have been carried out successfully in ionic liquids with tetrafluoroborate anion. The hydroformylation of functionalized and non-functionalized olefins is also possible with rhodium catalysts in ionic liquids with weakly coordinating anions (e.g. PF$_6$, BF$_4$) (Y. Chauvin, L. Mussmann, H. Olivier, European Patent, EP 776880, 1997; Y. Chauvin, L. Mussmann, H. Olivier, *Angew. Chem., Int. Ed Engl.*, 1995, 34, 2698; W. Keim, D. Vogt, H. Waffenschmidt, P. Wasserscheid, *J. of Cat.*, 1999, 186, 481).

Further important fields of application of ionic liquids consist of their use as extraction agents for material separation (J. G. Huddleston, H. D. Willauer, R. P. Swatlowski, A. E. Visser, R. D. Rogers, *Chem. Commun.* (1998), 1765-1766; b) A. E. Visser, R. P. Swatlowski, R. D. Rogers, *Green Chemistry* (2000), 2(1), 14) and of their use as heat carriers (M. L. Mutch, J. S. Wilkes, *Proceedings of the Eleventh International Symposium on Molten Salts*, P. C. Trulove, H. C. De Long, G. R. Stafford and S. Deki (Editors), Proceedings Volume 98-11, The Electrochemical Society, Inc, Pennington, N.J.; 1998, page 254).

Even if the definition of an ionic liquid includes those salts whose melting point is between room temperature and 100° C., it is still necessary and desirable for many applications for the ionic liquids to be liquid at temperatures below room temperature already.

Further, for all applications in which ionic liquids are used as solvents or solvent additives in the field of chemical synthesis or catalysis, but also as heat carriers or as extraction solvents, the use of very low viscosity ionic liquids is of high technical value. The lower the viscosity of the ionic liquids, the faster diffusion and mass transport processes occur in those applications. In most applications, this has direct consequences for the space-time yield that can be achieved, the energy requirements or the necessary amount of ionic liquids. To conclude, the economic efficiency of almost all applications of ionic liquids is essentially determined by their viscosity: the lower the viscosity of the ionic liquid employed, the greater the economic efficiency of a corresponding application.

Numerous examples of ionic liquids are known that are liquid at room temperature. However, as a rule these systems possess halide ions such as $F^-$, $Cl^-$, $Br^-$ or $I^-$ or those anions which contain halogen atoms, e.g. organohalides. Typical representatives of the latter anions include, by way of example and without limitation, $(BF_4)$, $(PF_6)$, $(CF_3CO_2)$, $(CF_3SO_3)$, $((CF_3SO_2)_2N)^-$, $(AlCl_4)^-$, $(Al_2Cl_7)^-$ or $(SnCl_3)^-$. The use of such anions containing halogen atoms imposes serious restrictions on the applicability of the corresponding ionic liquids:

a) The use of these anions leads to considerable costs since even the alkali salts of these ions are very expensive;

b) The hydrolysis products of these anions containing halogen atoms lead to considerable corrosion in steel reactors and in some instances also in glass reactors;

c) The thermal disposal of a "spent" ionic liquid with anions containing halogen atoms usually causes corrosion and environmental problems and is therefore very costly. Disposal via degradation in a biological clarification plant is also rendered difficult by the presence of anions containing halogen atoms.

In general, ionic liquids that are substantially free from halogen atoms (halogenic anions or organohalides) are therefore of particular interest, especially if they additionally possess the following properties:

a) a melting point and/or glass transition point of less than 25° C.;

b) a low viscosity (<0.8 Pas at 20° C. (800 cPs at 20° C.));

c) hydrolysis-stable in neutral aqueous solution (pH=7) up to 80° C.

Among the ionic liquids free from halogen atoms according to the state of the art, there have been no representatives so far capable of satisfying this complex technical requirement profile. Thus, nitrate melts, nitrite melts, sulfate melts (J. S. Wilkes, M. J. Zaworotko, *J. Chem. Soc. Chem. Commun.* (1992), 965) and benzenesulfonate melts (H. Waffenschmidt, Dissertation, RWTH Aachen 2000) are known, however, these ionic liquids have melting points above room temperature. Hydrogen sulfates and hydrogen phosphates react in aqueous solution while splitting off one or several protons and form acidic aqueous solutions. Methyl sulfate and ethyl sulfate melts exhibit a distinct hydrolysis after only 1 h at 80° C. in aqueous solution with the formation of hydrogen sulfate anions and the corresponding alcohol (compare also Comparative Examples 1 and 2). Ionic liquids of general formula (cation) (R—O—SO$_3$) have a viscosity higher than that required for use in most technical applications (see requirement b) if R merely represents a linear or branched, saturated or unsaturated, aliphatic or alicyclic alkyl group having 3-36 carbon atoms non-functionalized or functionalized with one or more groups Y, in which Y is an —OH, —OR", —COOH, —COOR", —NR$_2$, —SO$_4$, —F, —Cl, —Br, —I or —CN group, R″ representing a branched or linear hydrocarbon chain with 1-12 carbon atoms (see Comparative Example 3).

Therefore, it is the object of the present invention to provide halogen-free ionic liquids that have a melting point or glass point of 25° C. or lower, a viscosity of 0.8 Pas at 20° C. (800 cPs at 20° C.) or lower, and improved aqueous hydrolytic stability.

SUMMARY OF THE INVENTION

The present invention seeks to overcome one or more of the disadvantages of the prior art. In one aspect, the invention provides an ionic liquid comprising a compound of the formula:

(cation)(R′—O—SO₃)  (Formula I);

(cation)(R′—SO₃)  (Formula II); or a mixture of the two compounds;

wherein

R′ represents a group of general formula $R^5—(X(—CH_2—)_n)_m—$ in which n represents a number from 1 to 12;

m represents a number independent of n of from 1 to 400, preferably from 50 to 300, more preferably from 100 to 200;

X represents —O—, —S—, or a functionality of general form —O—Si(CH₃)₂—O—, —O—Si(CH₂CH₃)₂—O—, —O—Si(O—CH₃)₂—O—, —O—Si(O—CH₂CH₃)₂—O—; and $R^5$ represents a linear or branched, saturated or unsaturated, aliphatic or alicyclic alkyl group having 1-36 carbon atoms non-functionalized or functionalized with one or more groups Y, in which Y is an —OH, —OR″, —COOH, —COOR″, —NH₂, —SO₄, —F, —Cl, —Br, —I or —CN group, R″ representing a branched or linear hydrocarbon chain with 1-12 carbon atoms; and the (cation) is independently selected at each occurrence from the group consisting of:

quaternary ammonium cation of general formula $(NR^1R^2R^3R)^+$;

phosphonium cation of general formula $(PR^1R^2R^3R)^+$;

imidazolium cation of general formula

wherein the imidazole nucleus may be substituted with at least one group selected from $C_{1-6}$ alkyl, $C_{1-6}$ alkoxy, $C_{1-6}$ aminoalkyl, $C_{5-12}$ aryl or $C_{5-12}$-aryl-$C_{1-6}$-alkyl groups;

pyridinium cation of general formula

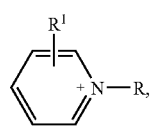

wherein the pyridine nucleus may be substituted with at least one group selected from $C_{1-6}$ alkyl, $C_{1-6}$ alkoxy, $C_{1-6}$ aminoalkyl, $C_{5-12}$ aryl or $C_{5-12}$-aryl-$C_{1-6}$-alkyl groups;

pyrazolium cation of general formula

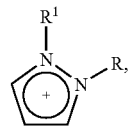

wherein the pyrazole nucleus may be substituted with at least one group selected from $C_{1-6}$ alkyl, $C_{1-6}$ alkoxy, $C_{1-6}$ aminoalkyl, $C_{5-12}$ aryl or $C_{5-12}$-aryl-$C_{1-6}$-alkyl groups; and triazolium cation of general formula

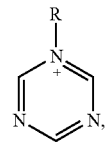

wherein the triazole nucleus may be substituted with at least one group selected from $C_{1-6}$ alkyl, $C_{1-6}$ alkoxy, $C_{1-6}$ aminoalkyl, $C_{5-12}$ aryl or $C_{5-12}$-aryl-$C_{1-6}$-alkyl groups; and the residues $R^1$, $R^2$, $R^3$ are independently selected at each occurrence from the group consisting of hydrogen;

linear or branched, saturated or unsaturated, aliphatic or alicyclic alkyl groups having from 1 to 20 carbon atoms;

oligoethylene glycol monoalkyl ethers of the form $(R^4—(O—CH_2—CH_2)_p—O—CH_2—CH_2)$, wherein p represents a number of from 1 to 30, preferably from 5 to 20, more preferably from 10 to 15, and $R^4$ represents a linear or branched, saturated or unsaturated, aliphatic or alicyclic alkyl group having 1 to 20, preferably 5 to 15, more preferably 8 to 12, carbon atoms;

heteroaryl, heteroaryl-$C_{1-6}$-alkyl groups having from 3 to 8 carbon atoms in the heteroaryl residue and at least one heteroatom selected from N, O and S which may be substituted with at least one group selected from Coo alkyl groups and/or halogen atoms;

aryl, aryl-$C_{1-6}$-alkyl groups having from 5 to 12 carbon atoms in the aryl residue which may be optionally substituted with at least one $C_{1-6}$ alkyl group and/or halogen atom; and the residue R is selected from linear or branched, saturated or unsaturated, aliphatic or alicyclic alkyl groups having 1 to 20, preferably 5 to 15, more preferably 8 to 12, carbon atoms;

oligoethylene glycol monoalkyl ethers of the form $(R^4—(O—CH_2—CH_2)_p—O—CH_2—CH_2)$, wherein p represents a number of from 1 to 30, preferably from 5 to 20, more preferably from 10 to 15, and $R^4$ represents a linear or branched, saturated or unsaturated, aliphatic or alicyclic alkyl group having 1 to 20, preferably 5 to 15, more preferably 8 to 12, carbon atoms;

heteroaryl-$C_{1-6}$-alkyl groups having from 3 to 8 carbon atoms in the aryl residue and at least one heteroatom selected from N, O and S which may be substituted with at least one $C_{1-6}$ alkyl group and/or halogen atoms;

aryl-$C_{1-6}$-alkyl groups having from 5 to 12 carbon atoms in the aryl residue which may be optionally substituted with at least one $C_{1-6}$ alkyl group and/or halogen atom.

In one aspect, the ionic liquid is a compound of the general formula (anion)(cation)  Formula III wherein
(cation) is independently selected at each occurrence from the definitions detailed herein or a mixture thereof; and
(anion) is independently selected as each occurrence from (R'—O—SO$_3$), (R'—SO$_3$) or a mixture thereof.

Specific embodiments of the ionic liquid of the invention include those wherein: 1) the (anion) is the same at each occurrence; 2) the (anion) is a mixture of two or more different (anions) described herein; 3) the (cation) is the same at each occurrence; 4) the (cation) is a mixture of two or more different (cations) described herein; 5) the ionic liquid is a mixture or two or more different ionic liquids.

When the ionic liquid is a mixture of two or more individual ionic liquids, the individual ionic liquids can have a (cation) in common or an (anion) in common. As used in this regard, the term "in common" means the two ionic liquids have (cations), for example, of the same type.

Another aspect of the invention provides an ionic liquid, as use thereof, of the formula (cation)(anion), wherein "cation" is as defined herein and "anion" is a compound of the Formula I, Formula II or a mixture thereof. When the ionic liquid is present as a mixture, the "cation" and "anion" are independently selected at each occurrence from the embodiments described herein.

In a preferred embodiment of the present invention, the ionic liquid comprises an anion of formula (Me(O—CH$_2$—CH$_2$)$_n$—O—SO$_3$), wherein n is a number of from 1 to 12, preferably 3, 4 or 5.

In a further preferred embodiment of the invention, the ionic liquid comprises an anion of formula (Me(O—CH$_2$—CH$_2$)$_n$—SO$_3$), wherein n is a number of from 1 to 12, preferably 2 or 3.

DETAILED DESCRIPTION OF THE INVENTION

The ionic liquids according to the invention are distinguished from the halogen-free ionic liquids of the prior art by a clearly reduced viscosity and very low melting points. Thus, these materials meet the above mentioned technically relevant combination of properties significantly better than all ionic liquids known in the prior art. In addition, the ionic liquids according to the invention are hydrolytically stable in a neutral aqueous solution (pH=7) up to 80° C. Moreover, the ionic liquids according to the invention have high thermal stabilities (up to above 250° C.).

As used herein in reference to an ionic liquid, the term "halogen-free" is intended to mean an ionic liquid containing no purposefully added ionic liquid molecule (i.e., the anion or cation of the invention) having a halogen atom. In other words, the ionic liquid comprising the anion and cation species does not contain halogen atoms. In particular, the organic residue of the anion and cation does not contain a halogen molecule. It is possible that an ionic liquid might contain some halide-based contaminant; however, any such contaminant will be present in an amount of less than 1% by wt., less than 0.5% by wt., or less than 0.1% by wt. of the ionic liquid. An ionic liquid meeting these requirements is said to be substantially halogen-free.

In particular, due to the combination of the halogen-free nature of the ionic liquids with a clearly reduced viscosity while the melting points are very low, which can be realized for the first time with the ionic liquids according to the invention, these novel ionic liquids are ideal substances for use as solvents, solvent additives for stoichiometric or catalytic chemical reactions as well as for their applications as extractants and/or heat carriers.

Therefore, further embodiments of the present invention relate to
- a process comprising the step of using the ionic liquid according to the invention as a solvent, solvent additive or phase-transfer catalyst. Such a process according to the invention can comprise reaction steps catalyzed by transition metals or enzymes or other biocatalysts, which reaction steps are preferably selected from hydroformylation reactions, oligomerization reactions and other C—C bond formation reactions, esterifications, isomerization reactions and reactions for amide bond formation;
- a process for the separation of materials comprising the step of using the ionic liquid according to the invention as a solvent or solvent additive;
- a device for heat exchange comprising an ionic liquid according to the invention as a heat carrier or heat carrier additive;
- the use of the ionic liquid according to the invention as a solvent or solvent additive;
- the use of the ionic liquid according to the invention as a phase-transfer catalyst;
- the use of the ionic liquid according to the invention as an extractant;
- the use of the ionic liquid according to the invention as a heat carrier; and
- the use of the ionic liquid according to the invention as an additive, as a surface-active substance, i.e., a detergent, as a modifier that alters the physicochemical properties of another liquid to which it is added, or as a softener or plasticizer.

In specific embodiments, the cation of the invention is a nitrogen-containing cation selected from the group consisting of a quaternary ammonium cation, an imidazolium cation, a pyridinium cation, a pyrazolium cation, a triazolium cation, and derivatives thereof. The cation can also be a phosphonium cation or a derivative thereof. In even more specific embodiments, each cation is as defined herein.

Ionic liquids that contain mixtures of different ionic liquids with the general (cation) (R'—O—SO$_3$) or (cation) (R'—SO$_3$) can also be produced and used according to the invention. Likewise, ionic liquid mixtures comprising different anions ((R'—O—SO$_3$) or (R'—SO$_3$)) but the same cations are be produced and used according to the invention. The invention also contemplates preparation and use of ionic liquid mixtures comprising different cations but the same anions. These systems can be prepared easily as described herein. Exemplary mixtures having technically interesting properties and comprising the same anion but different cations include, by way of example and without limitation, a mixture of (1-ethyl-3-methylimidazolium) (Me(O—CH$_2$—CH$_2$)$_2$—O—SO$_3$) and (1-butyl-3-methylimidazolium) (Me(O—CH$_2$—CH$_2$)$_2$—O—SO$_3$), a mixture of (1-butyl-3-methylimidazolium) (Me(O—CH$_2$—CH$_2$)$_2$—O—SO$_3$) and (1-butylpyridinium) (Me(O—CH$_2$—CH$_2$—CH$_2$)$_2$—O—SO$_3$), or a mixture of (1-ethyl-3-methylimidazolium) (Me(O—CH$_2$—CH$_2$)$_2$—O—SO$_3$) and (1-dodecyl-3-methylimidazolium) (Me(O—CH$_2$—CH$_2$)$_2$—O—SO$_3$).

The cations of the invention are readily available in free base form or in salt form from commercial suppliers. Alternatively, imidazolium (A. A. K. Abdul-Sada, P. W. Ambler, P.

K. G. Hodgson, K. R. Seddon, N.J. Steward, WO 95/21871, and *Chem. Abstr.* (1995), 123, P341298k), ammonium (R. H. Dubois, M. J. Zaworotko, P. S. White, *Inorg. Chem.* (1989), 28, 2019) and phosphonium (J. F. Knifton, *J. Mol. Catal.* (1987), 43, 65) cations are prepared according to well-known procedures such as those cited herein, the entire disclosures of which are hereby incorporated by reference.

Likewise, the anions, (R'—O—$SO_3$) or (R'—$SO_3$), of the invention are available in free acid or in salt form from commercial suppliers or they can be made as described herein.

The following compounds represent further preferred embodiments of the ionic liquids according to the invention:

(1-ethyl-3-methylimidazolium) (Me(O—$CH_2$—$CH_2$)$_2$—O—$SO_3$)
(1-ethyl-3-methylimidazolium) (Me(O—$CH_2$—$CH_2$)$_3$—O—$SO_3$)
(1-ethyl-3-methylimidazolium) (Me(O—$CH_2$—$CH_2$)$_4$—O—$SO_3$)
(1-ethyl-3-methylimidazolium) (Me(O—$CH_2$—$CH_2$)$_5$—O—$SO_3$)
(1-ethyl-3-methylimidazolium) (Me(O—$CH_2$—$CH_2$)$_2$—$SO_3$)
(1-ethyl-3-methylimidazolium) (Me(O—$CH_2$—$CH_2$)$_3$—$SO_3$)
(1-ethyl-3-methylimidazolium) (Et(O—$CH_2$—$CH_2$)$_2$—O—$SO_3$)
(1-ethyl-3-methylimidazolium) (Et(O—$CH_2$—$CH_2$)$_3$—O—$SO_3$)
(1-ethyl-3-methylimidazolium) (Et(O—$CH_2$—$CH_2$)$_4$—O—$SO_3$)
(1-ethyl-3-methylimidazolium) (Et(O—$CH_2$—$CH_2$)$_5$—O—$SO_3$)
(1-ethyl-3-methylimidazolium) (Et(O—$CH_2$—$CH_2$)$_2$—$SO_3$)
(1-ethyl-3-methylimidazolium) (Et(O—$CH_2$—$CH_2$)$_3$—$SO_3$)
(1-butyl-3-methylimidazolium) (Me(O—$CH_2$—$CH_2$)$_2$—O—$SO_3$)
(1-butyl-3-methylimidazolium) (Me(O—$CH_2$—$CH_2$)$_3$—O—$SO_3$)
(1-butyl-3-methylimidazolium) (Me(O—$CH_2$—$CH_2$)$_4$—O—$SO_3$)
(1-butyl-3-methylimidazolium) (Me(O—$CH_2$—$CH_2$)$_5$—O—$SO_3$)
(1-butyl-3-methylimidazolium) (Me(O—$CH_2$—$CH_2$)$_2$—$SO_3$)
(1-butyl-3-methylimidazolium) (Me(O—$CH_2$—$CH_2$)$_3$—$SO_3$)
(1-butyl-3-methylimidazolium) (Et(O—$CH_2$—$CH_2$)$_2$—O—$SO_3$)
(1-butyl-3-methylimidazolium) (Et(O—$CH_2$—$CH_2$)$_3$—O—$SO_3$)
(1-butyl-3-methylimidazolium) (Et(O—$CH_2$—$CH_2$)$_4$—O—$SO_3$)
(1-butyl-3-methylimidazolium) (Et(O—$CH_2$—$CH_2$)$_5$—O—$SO_3$)
(1-butyl-3-methylimidazolium) (Et(O—$CH_2$—$CH_2$)$_2$—$SO_3$)
(1-butyl-3-methylimidazolium) (Et(O—$CH_2$—$CH_2$)$_3$—$SO_3$)
(1-octyl-3-methylimidazolium) (Me(O—$CH_2$—$CH_2$)$_2$—O—$SO_3$)
(1-octyl-3-methylimidazolium) (Me(O—$CH_2$—$CH_2$)$_3$—O—$SO_3$)
(1-octyl-3-methylimidazolium) (Me(O—$CH_2$—$CH_2$)$_4$—O—$SO_3$)
(1-octyl-3-methylimidazolium) (Me(O—$CH_2$—$CH_2$)$_5$—O—$SO_3$)
(1-octyl-3-methylimidazolium) (Me(O—$CH_2$—$CH_2$)$_2$—$SO_3$)
(1-octyl-3-methylimidazolium) (Me(O—$CH_2$—$CH_2$)$_3$—$SO_3$)
(1-octyl-3-methylimidazolium) (Et(O—$CH_2$—$CH_2$)$_2$—O—$SO_3$)
(1-octyl-3-methylimidazolium) (Et(O—$CH_2$—$CH_2$)$_3$—O—$SO_3$)
(1-octyl-3-methylimidazolium) (Et(O—$CH_2$—$CH_2$)$_4$—O—$SO_3$)
(1-octyl-3-methylimidazolium) (Et(O—$CH_2$—$CH_2$)$_5$—O—$SO_3$)
(1-octyl-3-methylimidazolium) (Et(O—$CH_2$—$CH_2$)$_2$—$SO_3$)
(1-octyl-3-methylimidazolium) (Et(O—$CH_2$—$CH_2$)$_3$—$SO_3$)
(1-dodecyl-3-methylimidazolium) (Me(O—$CH_2$—$CH_2$)$_2$—O—$SO_3$)
(1-dodecyl-3-methylimidazolium) (Me(O—$CH_2$—$CH_2$)$_3$—O—$SO_3$)
(1-dodecyl-3-methylimidazolium) (Me(O—$CH_2$—$CH_2$)$_4$—O—$SO_3$)
(1-dodecyl-3-methylimidazolium) (Me(O—$CH_2$—$CH_2$)$_5$—O—$SO_3$)
(1-dodecyl-3-methylimidazolium) (Me(O—$CH_2$—$CH_2$)$_2$—$SO_3$)
(1-dodecyl-3-methylimidazolium) (Me(O—$CH_2$—$CH_2$)$_3$—$SO_3$)
(1-dodecyl-3-methylimidazolium) (Et(O—$CH_2$—$CH_2$)$_2$—O—$SO_3$)
(1-dodecyl-3-methylimidazolium) (Et(O—$CH_2$—$CH_2$)$_3$—O—$SO_3$)
(1-dodecyl-3-methylimidazolium) (Et(O—$CH_2$—$CH_2$)$_4$—O—$SO_3$)
(1-dodecyl-3-methylimidazolium) (Et(O—$CH_2$—$CH_2$)$_5$—O—$SO_3$)
(1-dodecyl-3-methylimidazolium) (Et(O—$CH_2$—$CH_2$)$_2$—$SO_3$)
(1-dodecyl-3-methylimidazolium) (Et(O—$CH_2$—$CH_2$)$_3$—$SO_3$)
(1-methylimidazolium) (Me(O—$CH_2\,CH_2$)—$SO_3$)
(1-methylimidazolium) (Me(O—$CH_2$—$CH_2$)$_3$—O—$SO_3$)
(1-methylimidazolium) (Me(O—$CH_2$—$CH_2$)$_4$—O—$SO_3$)
(1-methylimidazolium) (Me(O—$CH_2$—$CH_2$)$_5$—O—$SO_3$)
(1-methylimidazolium) (Me(O—$CH_2$—$CH_2$)$_2$—$SO_3$)
(1-methylimidazolium) (Me(O—$CH_2$—$CH_2$)$_3$—$SO_3$)
(1-methylimidazolium) (Et(O—$CH_2$—$CH_2$)$_2$—O—$SO_3$)
(1-methylimidazolium) (Ft(O—$CH_2$—$CH_2$)$_3$—O—$SO_3$)
(1-methylimidazolium) (Et(O—$CH_2$—$CH_2$)$_4$—O—$SO_3$)
(1-methylimidazolium) (Et(O—$CH_2$—$CH_2$)$_5$—O—$SO_3$)
(1-methyl imidazolium) (Et(O—$CH_2$—$CH_2$)$_2$—$SO_3$)
(1-methylimidazolium) (Et(O—$CH_2$—$CH_2$)$_3$—$SO_3$)
(pyridinium) (Me(O—$CH_2C_2$)$_2$—$SO_3$)
(pyridinium) (Me(O—$CH_2$—$CH_2$)$_3$—O—$SO_3$)
(pyridinium) (Me(O—$CH_2$—$CH_2$)$_4$—O—$SO_3$)
(pyridinium) (Me(O—$CH_2$—$CH_2$)$_5$—O—$SO_3$)
(pyridinium) (Me(O—$CH_2$—$CH_2$)$_2$—$SO_3$)
(pyridinium) (Me(O—$CH_2$—$CH_2$)$_3$—$SO_3$)
(pyridinium) (Et(O—$CH_2$—$CH_2$)$_2$—O—$SO_3$)
(pyridinium) (Et(O—$CH_2$—$CH_2$)$_3$—O—$SO_3$)
(pyridinium) (Et(O—$CH_2$—$CH_2$)$_4$—O—$SO_3$)
(pyridinium) (Et(O—$CH_2$—$CH_2$)$_5$—O—$SO_3$)
(pyridinium) (Et(O—$CH_2$—$CH_2$)$_2$—$SO_3$)
(pyridinium) (Et(O—$CH_2$—$CH_2$)$_3$—$SO_3$)
(1-butylpyridinium) (Me(O—$CH_2$—$CH_{22}$—O—$SO_3$)

(1-butylpyridinium) (Me(O—CH$_2$—CH$_2$)$_3$—O—SO$_3$)
(1-butylpyridinium) (Me(O—CH$_2$—CH$_2$)$_4$—O—SO$_3$)
(1-butylpyridinium) (Me(O—CH$_2$—CH$_2$)$_5$—O—SO$_3$)
(1-butylpyridinium) (Me(O—CH$_2$—CH$_{22}$—SO$_3$)
(1-butylpyridinium) (Me(O—CH$_2$—CH$_2$)$_3$—SO$_3$)
(1-butylpyridinium) (Et(O—CH$_2$—CH$_{22}$—O—SO$_3$)
(1-butylpyridinium) (Et(O—CH$_2$—CH$_2$)$_3$—O—SO$_3$)
(1-butylpyridinium) (Et(O—CH$_2$—CH$_2$)$_4$—O—SO$_3$)
(1-butylpyridinium) (Et(O—CH$_2$—CH$_2$)$_5$—O—SO$_3$)
(1-butylpyridinium) (Et(O—CH$_2$—CH$_{22}$—SO$_3$)
(1-butylpyridinium) (Et(O—CH$_2$—CH$_2$)$_3$—SO$_3$)
(trioctylmethylammonium) (Me(O—CH$_2$—CH$_{22}$—O—SO$_3$)
(trioctylmethylammonium) (Me(O—CH$_2$—CH$_2$)$_3$—O—SO$_3$)
(trioctylmethylammonium) (Me(O—CH$_2$—CH$_2$)$_4$—O—SO$_3$)
(trioctylmethylammonium) (Me(O—CH$_2$—CH$_2$)$_5$—O—SO$_3$)
(trioctylmethylammonium) (Me(O—CH$_2$—CH$_2$)$_2$—SO$_3$)
(trioctylmethylammonium) (Me(O—CH$_2$—CH$_2$)$_3$—SO$_3$)
(trioctylmethylammonium) (Et(O—CH$_2$—CH$_2$)$_2$—O—SO$_3$)
(trioctylmethylammonium) (Et(O—CH$_2$—CH$_2$)$_3$—O—SO$_3$)
(trioctylmethylammonium) (Et(O—CH$_2$—CH$_2$)$_4$—O—SO$_3$)
(trioctylmethylammonium) (Et(O—CH$_2$—CH$_2$)$_5$—O—SO$_3$)
(trioctylmethylammonium) (Et(O—CH$_2$—CH$_2$)$_2$—SO$_3$)
(trioctylmethylammonium) (Et(O—CH$_2$—CH$_2$)$_3$—SO$_3$)

Specific exemplary embodiments of the cation include (1,3-dimethylimidazolium), (1-ethyl-3-methylimidazolium), (1-propyl-3-methylimidazolium), (1-ethyl-2,3-dimethylimidazolium), (1-butyl-2,3-dimethylimidazolium), (1,2-dimethyl-3-octylimidazolium), (1-butyl-3-methylimidazolium), (1-methylimidazolium), (1-ethylimidazolium), (1-butylimidazolium), (1-octylimidazolium), (1-hexyl-3-methylimidazolium), (1-octyl-3-methylimidazolium), (1-dodecyl-3-methylimidazolium), (1-methylpyridinium), (1-ethylpyridinium), (1-butylpyridinium), (pyridinium), (trioctylmethylammonium), and (trioctylmethylphosphonium).

Specific exemplary embodiments of the anion include (Me(O—CH$_2$—CH$_2$)$_2$—O—SO$_3$), (Me(O—CH$_2$—CH$_2$)$_3$—O—SO$_3$), (Me(O—CH$_2$—CH$_2$)$_4$—O—SO$_3$), (Ne(O—CH$_2$—CH$_2$)$_5$—O—SO$_3$), (Me(O—CH$_2$—CH$_2$)$_2$—SO$_3$), (Me(O—CH$_2$—CH$_2$)$_5$—SO$_3$), (Et(O—CH$_2$—CH$_2$)$_5$—O—SO$_3$), (Et(O—CH$_2$—CH$_2$)$_3$—O—SO$_3$), (Et(O—CH$_2$—CH$_2$)—O—SO$_3$), (Et(O—CH$_2$—CH$_2$)$_5$—O—SO$_3$), (Et(O—CH$_2$—CH$_2$)—SO$_3$), (Et(O—CH$_2$—CH$_2$)$_3$—SO$_3$), (Bu(O—CH$_2$—CH$_2$)$_2$—O—SO$_3$), (Bu(O—CH$_2$—CH$_2$)$_3$—O—SO$_3$), (Bu(O—CH$_2$—CH$_2$)—O—SO$_3$), (Bu(O—CH$_2$—CH$_2$)$_5$—O—SO$_3$), (Bu(O—CH$_2$—CH$_2$)$_2$—SO$_3$), (Bu(O—CH$_2$—CH$_2$)$_3$—SO$_3$), (Et(S—CH$_2$—CH$_2$)$_2$—O—SO$_3$), and (Et(O—Si(CH$_3$)$_2$—O—CH$_2$—CH$_2$)$_2$—O—SO$_3$).

As used herein, the following terms are defined as noted: "Me" means methyl; "Et" means ethyl; "Bu" means butyl, "Pr" means propyl.

The ionic liquid of the invention can be made according to the processes described herein. General synthetic schemes are detailed below.

Scheme 1 details a general synthetic process, a particular embodiment of which is exemplified in Synthetic Example 1 and Synthetic Example 2.

SCHEME 1

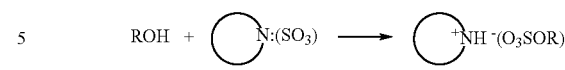

In this case, an organic amine-SO$_3$ complex is treated with a hydroxide-containing molecule (e.g. ROH), optionally in the presence of heating, and optionally at reduced, ambient, or elevated pressure, for a period of time sufficient to form the ionic liquid.

Scheme 2 details a general synthetic process, a particular embodiment of which is exemplified in Synthetic Example 3 (method 1) and Synthetic Example 4 (method 1).

SCHEME 2

The ionic liquid of Example 1 is treated with an aromatic or alkyl quaternary amine salt, optionally at reduced, ambient or elevated temperature, and optionally at reduced, ambient or elevated pressure, for a sufficient period of time to form the ionic liquid, wherein the amine from the first ionic liquid has been removed. That removal can be done by a number of different methods as described herein, e.g. sublimation, precipitation, distillation, and/or extraction. The group "G" indicated in Scheme 2 corresponds with the remaining structures of the cationic groups detailed herein for the ionic liquid. A key requirement for this synthetic scheme is that a primary, secondary, or tertiary amine-based ionic liquid is treated with a quaternary ammonium salt to form another ionic liquid.

Scheme 3 details a general synthetic process, a particular embodiment of which is exemplified in Synthetic Example 3 (method 2) and Synthetic Example 4 (method 2).

SCHEME 3

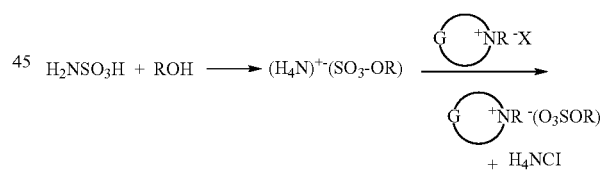

Sulfamic acid is treated with a hydroxide-containing molecule, optionally at reduced, ambient or elevated temperature, and optionally at reduced, ambient or elevated pressure, for a sufficient period of time to form an ionic liquid intermediate. The intermediate is treated with another more basic amine-containing molecule to form the desired ionic liquid or an intermediate which is finally converted into the final ionic liquid according to the invention, wherein the amine from the first ionic liquid has been removed as noted above. In Scheme 3, for example, the intermediate ionic liquid (H$_4$N)(SO$_3$—OR) is treated with a quaternary ammonium salt to form the final ionic liquid and the byproduct H$_4$Cl, which is removed by extraction or precipitation or as described herein. A key requirement for this synthetic scheme is that ammonium cation is replaced with a quaternary ammonium salt to form another ionic liquid.

The stability of the ionic liquids of the invention is determined by exposing the ionic liquid to hydrolytic conditions. An aliquot of the ionic liquid is placed in a volume of water and the mixture is heated. The pH of the mixture is measured periodically. If the pH remains approximately neutral even after an extended period of time (e.g. 2 hours or more), then the ionic liquid is said to be hydrolytically stable. If the pH becomes more acidic after an extended period of time as compared to the initial pH of the solution, then the ionic liquid is being hydrolyzed to form an acidic species and the ionic liquid is not hydrolytically stable. Comparative Example 1 and 2 detail evaluations of sulfate salts that are not made according to the invention. Specifically the salt is exposed to hydrolytic testing conditions as used for the ionic liquid of the invention. The salts are rapidly hydrolyzed under the same test conditions (80° C., atmospheric pressure, in an open vessel for a period of at least two hours). Exemplary evaluations of the hydrolytic stability of the ionic liquids are detailed below.

Characterization Example 3 details the results for viscosity measurements of the ionic liquid 1-ethyl-3-methylimidazolium methylsulfate. The measurement was conducted in HAAKE RS 100 rheometer. The data demonstrate that the ionic liquids of the invention have a very low viscosity.

As noted above, the ionic liquid can be used in many different process applications. Method of Use Example 1 details an exemplary process for conducting hydroformylation of 1-octene use (1-butyl-3-methylimidazolium) (Me(O—$CH_2$—$CH_2$)$_2$—O—$SO_3$) (according to the invention) as the solvent, and Comparative Method of Use Example 1 details an exemplary process for conducting hydroformylation of 1-octene use (1-butyl-3-methylimidazolium) ($C_8H_{17}$—O—$SO_3$) (not according to the invention) as the solvent. In this case, the $C_8H_{17}$— residue is a straight chain non-functionalized alkyl group. As noted in the results, the ionic liquid of the invention provided an improved (48.8% versus 15.6%) overall conversion of 1-octene to the aldehyde even though the reactions were conducted under substantially the same conditions. Moreover, the ionic liquid of the invention provided a higher turnover frequency for the catalyst: 480 versus 160. This is true even though the ratio of linear aldehydes to branched aldehydes is about the same for both ionic liquids.

Similar positive effects are observed in other liquid-liquid biphasic reactions where the lower viscosity of (1-butyl-3-methylimidazolium) (Me(O—$CH_2$—$CH_2$)$_2$—O—$SO_3$) vs. (1-butyl-3-methylimidazolium)($C_8H_{17}$—O—$SO_3$) leads to faster mass transfer between the two liquid phases and therefore to a higher overall reaction rate. Further examples are the Pd-catalyzed oligomerization of 1-butene where the overall activity of the liquid-liquid reaction system is increased by a factor 2.5 by replacing (1-butyl-3-methylimidazolium) ($C_8H_{17}$—O—$SO_3$) with (1-butyl-3-methylimidazolium) (Me(O—$CH_2$—$CH_2$)—O—$SO_3$) and performing the reaction under otherwise identical conditions. In the acid catalyzed esterification of acetic acid with hexanol, the overall activity of the liquid-liquid reaction system is increased by a factor 2.8 by replacing (1-butyl-3-methylimidazolium) ($C_8H_{17}$—O—$SO_3$) with (1-butyl-3-methylimidazolium) (Me(O—$CH_2$—$CH_2$)$_2$—O—$SO_3$) under otherwise identical reaction conditions. In the acid catalyzed isomerization of 1-octene, the overall activity of the liquid-liquid reaction system is increased by a factor 1.8 by replacing (1-butyl-3-methylimidazolium)($C_8H_{17}$—O—$SO_3$) with (1-butyl-3-methylimidazolium) (Me(O—$CH_2$—$CH_2$)$_2$—O—$SO_3$) under otherwise identical reaction conditions. In the enzyme catalyzed transesterification of vinyl acetate with 1-phenylethanol, the overall activity of the reaction system is increased by a factor 1.6 by replacing (1-butyl-3-methylimidazolium) ($C_8H_{17}$—O—$SO_3$) with (1-butyl-3-methylimidazolium) (Me(O—$CH_2$—$CH_2$)$_2$—O—$SO_3$) under otherwise identical reaction conditions. The additional functional groups in the ionic liquids according to this invention provide specific flexibility for the structural optimization of these ionic liquids for their use as plasticizers for polyacrylates and polyamides as well as for their use as detergents.

The ionic liquid of the invention can be used in almost any reaction wherein it can aid in the reaction or improve reaction conditions. For example, the ionic liquid can be used in a hydroformylation reaction, oligomerization reaction, esterification reaction, isomerization reaction, C—C bond-forming reaction, or amide bond-forming reaction. The ionic liquid can be used in a transition metal catalyzed, enzyme catalyzed or biocatalyst catalyzed chemical reaction. For example, an enzyme catalyzed esterification reaction is conducted in the presence of the reactants, enzyme, solvent and the ionic liquid, whereby it improves the results obtained with the enzyme catalyzed reaction.

Another aspect of the invention provides use of the ionic liquid as a solvent additive. In this case, the ionic liquid is added to a solvent or mixture of solvents, wherein its desired properties or functionalities are exploited. As a solvent additive, the ionic liquid can alter the properties of the solvent to form a more advantageous mixture.

According to another aspect of the invention, the ionic liquid is used as a solvent. In the liquid form, the ionic liquid can serve as an extraction solvent, whereby one or more compounds are extracted from a solid, semisolid or liquid. In this case, a solid, semisolid or liquid is exposed to the ionic liquid for a sufficient period of time and at a temperature sufficient to extract the desired compound(s) from the solid, semisolid or liquid. The ionic liquid will generally be substantially immiscible with the other liquid or solid (i.e., the other phase) from which the desired extract will be obtained. In this case, one or more other compounds are dissolved with the ionic liquid while in the liquid state. Depending upon the melting point of the ionic liquid, heat may have to be employed to render it a liquid.

Since it is a low melting material and it does not corrode metal or synthetic conduits significantly, the ionic liquid can serve as a heat carrier liquid when it is melted. In this case, the molten ionic liquid can conduct heat from one area of a heat exchange unit to another area. For example, a heat exchange unit is operably attached to a vessel. The heat exchange unit containing the ionic liquid heats the compound that is then conducted via conduit to a jacket surrounding or within the vessel. The vessel removes some of the heat from the liquid, which the returns to the heat exchange unit for reheating. By way of this recirculation, the ionic liquid conducts heat from the heat exchanger to the vessel. In a similar fashion, the ionic liquid can be recirculated to remove heat from the vessel. When used as a heat carrier additive, the ionic liquid alters/improves the properties/performance of a first heat carrier.

The invention will be further illustrated by the following Examples without being restricted to these Examples. In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

Synthetic Example 1

(pyridinium) (Me(O—CH$_2$—CH$_2$)$_2$O—SO$_3$)

To a solution of 10.48 g (87.22 mmol) of diethylene glycol monomethyl ether, 13.9 g of pyridine-SO$_3$ complex (87.22 mmol) is added in small portions at 0° C. The reaction mixture is further stirred at 25° C. for 18 hours. The product is obtained in quantitative yield in the form of a yellowish liquid with a surprisingly low viscosity. The melting point of the substance is below 20° C.

NMR:
$^1$H-NMR (300 MHz, CDCl$_3$): δ=9.03 (d, 2H, CH—(CH—CH)$_2$—N), 8.71 (m, 1H, CH—(CH—CH)$_2$—N), 8.20 (m, 2H, CH—(CH—CH)$_2$—N), 4.25 (tr, 2H, O$_3$—S—O—CH$_2$—CH$_2$—O—CH$_2$—CH$_2$—O—CH$_3$), 3.69 (tr, 2H, O$_3$—S—O—CH$_2$—CH$_2$—O—CH$_2$—CH$_2$—O—CH$_3$), 3.66 (tr, 2H, O$_3$—S—O—CH$_2$—CH$_2$—O—CH$_2$—CH$_2$—O—CH$_3$), 3.54 (tr, 2H, O$_3$—S—O—CH$_2$—CH$_2$—O—CH$_2$—CH$_2$—O—CH$_3$), 3.32 (s, 3H, O$_3$—S—O—CH$_2$—CH$_2$—O—CH$_2$—CH$_2$—O—CH$_3$) ppm.
$^{13}$C-NMR (75 MHz, CDCl$_3$): δ=147.1, 142.0, 127.8, 71.7, 70.1, 69.5, 66.8, 58.7 ppm.

A general synthetic scheme for this example is depicted in Scheme 1.

Synthetic Example 2

(pyridinium) (Me(O—CH$_2$—CH$_2$)$_3$—O—SO$_3$)

To a solution of 20.87 g (127.1 mmol) of triethylene glycol monomethyl ether, 20.23 g of pyridine-SO$_3$ complex (127.1 mmol) is added in small portions at 0° C. The reaction mixture is further stirred at 25° C. for 18 hours. The product is obtained in quantitative yield in the form of an almost colorless liquid. The melting point of the substance is below 20° C. A general synthetic scheme for this example is depicted in Scheme 1.

NMR:
$^1$H-NMR (300 MHz, CDCl$_3$): δ=9.02 (d, 2H, CH—(CH—CH)$_2$—N), 8.71 (m, 1H, CH—(CH—CH)$_2$—N), 8.24 (m, 2H, CH—(CH—CH)$_2$—N), 4.25 (tr, 2H, O$_3$—S—O—CH$_2$—CH$_2$—O—CH$_2$—CH$_2$—O—CH$_2$—CH$_2$—O—CH$_3$), 3.77 (tr, 2H, O$_3$—S—O—CH$_2$—CH$_2$—O—CH$_2$—CH$_2$—O—CH$_2$—CH$_2$—O—CH$_3$), 3.65 (m, 6H, O$_3$—S—O—CH$_2$—CH$_2$—O—CH$_2$—CH$_2$—O—CH$_2$—CH$_2$—O—CH$_3$), 3.53 (tr, 2H, O$_3$—S—O—CH$_2$—CH$_2$—O—CH$_2$—CH$_2$—O—CH$_2$—CH$_2$—O—CH$_3$), 3.32 (s, 3H, O$_3$—S—O—CH$_2$—CH$_2$—O—CH$_2$—CH$_2$—O—CH$_2$—CH$_2$—O—CH$_3$) ppm.
$^{13}$C-NMR (75 MHz, CDCl$_3$): δ=147.1, 142.0, 127.8, 71.6, 70.3-70.1, 69.6, 66.8, 58.8 ppm.

Synthetic Example 3

(1-butyl-3-methylimidazolium) (Me(O—CH$_2$—CH$_2$)$_2$—O—SO$_3$)
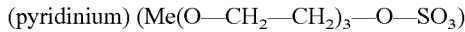

Method 1:
In a sublimation apparatus, 21.88 g of (pyridinium) (Me(O—CH$_2$—CH$_2$)$_2$—O—SO$_3$) (78.33 mmol) (prepared by the method as described in Synthetic Example 1) and 13.68 g of (1-butyl-3-methylimidazolium)Cl (78.33 mmol) are heated at 80° C. under vacuum. Under these conditions, (pyridinium)Cl sublimes from the reaction mixture to precipitate on the cooling surfaces of the sublimation apparatus in the form of white needles. After 8 h, the (pyridinium)Cl is completely removed from the reaction mixture, and the liquid yellowish product with a surprisingly low viscosity can be removed from the sublimation apparatus in quantitative yield. The melting point of the substance is below 20° C. A general synthetic scheme for this example is depicted in Scheme 2.

Method 2:
37.13 g of diethylene glycol monomethyl ether (308.99 mmol) and 30.0 g of sulfamic acid (308.99 mmol) are added to a 250 ml Schlenk flask and heated at 85° C. with stirring for 18 h under an inert gas atmosphere. The salt (NH$_4$) (O$_3$S—CH$_2$—CH$_2$—CH$_2$—CH$_2$-Me) is formed in quantitative yield in the form of a clear viscous yellowish liquid. At room temperature, this intermediate product is admixed with 53.97 g of (1-butyl-3-methylimidazolium)Cl (308.99 mmol) dissolved in 300 ml of dry CH$_2$Cl$_2$, and the mixture is intensively intermixed. The precipitate of NH$_4$Cl is filtered off through a fine frit under inert gas, and the clear filtrate is concentrated. The product is obtained with more than 95% yield in the form of a slightly yellow-brownish low-viscous liquid. The melting point of the substance is below 20° C.

NMR:
$^1$H-NMR (300 MHz, CDCl$_3$): δ=9.36 (s, 1H, N—CH—N), 7.62, 7.55 (s each, 1H each, N—CH), 4.25 (tr, 2H, N—CH$_2$—CH$_2$—CH$_2$CH$_3$), 4.16 (tr, 2H, O$_3$—S—O—CH$_2$—CH$_2$—O—CH$_2$—CH$_2$—O—CH$_3$), 4.01 (s, 3H, N—CH$_3$), 3.74 (tr, 2H, O$_3$—S—O—CH$_2$—CH$_2$—O—CH$_2$—CH$_2$—O—CH$_3$), 3.63 (tr, 2H, O$_3$—S—O—CH$_2$—CH$_2$—O—CH$_2$—CH$_2$—O—CH$_3$), 3.51 (tr, 2H, O$_3$—S—CH$_2$—CH$_2$—O—CH$_2$—CH$_2$—O—CH$_3$), 3.33 (s, 3H, O$_3$—S—O—CH$_2$—CH$_2$—O—CH$_2$—CH$_2$—O—CH$_3$), 1.87 (mult., 21, N—CH$_2$—CH$_2$—CH$_2$—CH$_3$), 1.37 (mult., 2H, N—CH$_2$—CH$_2$—CH$_2$—CH$_3$), 0.94 (tr, 3H, N—CH$_2$—CH$_2$—CH$_2$—CH$_3$) ppm.
$^{13}$C-NMR (75 MHz, d$^6$-CDCl$_3$): δ=137.1, 124.0, 122.8, 71.8, 70.2, 69.9, 66.3, 58.8, 49.5, 36.2, 32.0, 19.3, 13.4 ppm.

Viscosity

The following viscosities were determined for (1-butyl-3-methylimidazolium) (Me(O—CH$_2$—CH$_2$)$_2$—O—SO$_3$)
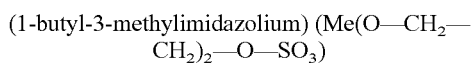

20° C.; η=639 cP±10 cP

40° C.; η=93 cP±3 cP

60° C.; η=64 cP±3 cP

80° C.; η=32 cP±2 cP

Hydrolysis Experiment:

5 g of the ionic liquid (1-butyl-3-methylimidazolium) (Me(O—CH$_2$—CH$_2$)$_2$—O—SO$_3$) is admixed with 5 ml of water, and the mixture is heated to 80° C. At 10 min intervals, samples are taken from the reaction solution, and pH measurements are performed. Even after 2 h at 80° C., the reaction solution is pH neutral, which leads one to conclude that no hydrolytic decomposition of the ionic liquid occurs under such reaction conditions.

Synthetic Example 4

(1-octyl-3-methylimidazolium) (Me(O—CH$_2$—CH$_2$)$_2$—O—SO$_3$)

Method 1:

In a sublimation apparatus, 21.88 g of (pyridinium) (Me(O—CH$_2$—CH$_2$)$_2$—O—SO$_3$) (78.33 mmol) is dissolved in 100 ml of distilled water, and 3.13 g of NaOH (78.33 mmol) is added in small portions with cooling. The aqueous solution is stirred at room temperature for 15 min and then extracted three times with 200 ml each of ether.

Subsequently, the aqueous solution is combined with 21.56 g of (1-octyl-3-methylimidazolium)Cl (78.33 mmol) dissolved in 100 ml of water. The aqueous phase is extracted three times with 200 ml each of CH$_2$Cl$_2$, the combined organic phases are dried over Na$_2$SO$_4$, and the solvent is removed under vacuum. The product is obtained with more than 95% yield in the form of a slightly yellowish liquid. The melting point of the substance is below 20° C.

Method 2:

37.13 g of diethylene glycol monomethyl ether (308.99 mmol) and 30.0 g of sulfamic acid (308.99 mmol) are added to a 250 ml Schlenk flask and heated at 85° C. with stirring for 18 h under an inert gas atmosphere. The salt (NH$_4$) (O$_3$S—O—CH$_2$—CH$_2$—O—CH$_2$—CH$_2$—O-Me) is formed in quantitative yield in the form of a clear viscous yellowish liquid. At room temperature, this intermediate product is dissolved in 100 ml of distilled water and combined with a solution of 85.04 g of (1-octyl-3-methylimidazolium)Cl (308.99 mmol) in 100 ml of water. The aqueous phase is extracted three times with 200 ml each of CH$_2$Cl$_2$, the combined organic phases are dried over Na$_2$SO$_4$, and the solvent is removed under vacuum. The product is obtained with more than 95% yield in the form of a slightly yellowish liquid. The melting point of the substance is below 20° C.

NMR:

1H-NMR (300 MHz, CDCl$_3$): δ=9.64 (s, 1H, N—CH—N), 7.74, 7.60 (s each, 1H each, N—CH), 4.32 (tr, 2H, N—CH$_2$—CH$_2$—(CH$_2$)$_5$—CH$_3$), 4.18 (tr, 2H, O$_3$—S—O—CH$_2$—CH$_2$—O—CH$_2$—CH$_2$—O—CH$_3$), 4.08 (s, 3H, N—CH$_3$), 3.73 (tr, 2H, O$_3$—S—O—CH, —CH$_2$—O—CH, —CH$_2$—O—CH$_3$), 3.63 (tr, 2H, O$_3$—S—O—CH$_2$—CH$_2$—O—CH$_2$—CH$_2$—O—CH$_3$), 3.53 (tr, 2H, O$_3$—S—O—CH$_2$—CH$_2$—O—CH$_2$—CH$_2$—O—CH$_3$), 3.34 (s, 3H, O$_3$—S—O—CH$_2$—CH$_2$—O—CH$_2$—CH$_2$—O—CH$_3$), 1.91 (tr, 2H, N—CH$_2$—CH$_2$—(CH$_2$)$_5$—CH$_3$); 1.30 (m, 10H, N—CH$_2$—CH$_2$—(CH$_2$)$_5$—CH$_3$); 0.86 (tr, 3H, N—CH$_2$—CH$_2$—(CH$_2$)$_5$—CH$_3$) ppm.

13C-NMR (75 MHz, d6-CDCl$_3$): δ=137.0, 124.0, 122.3, 71.6, 70.0, 69.8, 66.5, 58.8, 49.9, 36.4, 31.7, 30.2, 29.0, 28.9, 26.1, 22.5, 14.1 ppm.

Hydrolysis Experiment:

5 g of the ionic liquid (1-octyl-3-methylimidazolium) (Me(O—CH$_2$—CH$_2$)$_2$—O—SO$_3$) is admixed with 5 ml of water, and the mixture is heated to 80° C. At 10 min intervals, samples are taken from the reaction solution, and pH measurements are performed. Even after 2 h at 80° C., the reaction solution is pH neutral, which leads one to conclude that no hydrolytic decomposition of the ionic liquid occurs under such reaction conditions.

Comparative Example 1

Hydrolysis Experiment with 1-n-butyl-3-methylimidazolium Methylsulfate ((BMIM) (CH$_3$SO$_4$))

5 g of the ionic liquid 1-n-butyl-3-methylimidazolium methylsulfate ((BMIM) (CH$_3$SO$_4$)) is admixed with 5 ml of water, and the mixture is heated to 80° C. At 10 min intervals, samples are taken from the reaction solution, and pH measurements are performed. Already from the first measurement, a fast decrease of the pH value down to pH 1-2 is found. This leads one to conclude that hydrolytic decomposition of the ionic liquid occurs under such reaction conditions to release methanol and the acidic hydrogensulfate anion.

Comparative Example 2

Hydrolysis Experiment with 1-ethyl-3-methylimidazolium methylsulfate ((EMIM) (C$_2$H$_5$SO$_4$))

5 g of the ionic liquid 1-ethyl-3-methylimidazolium methylsulfate ((EMM) (C$_2$H$_5$SO$_4$)) is admixed with 5 ml of water, and the mixture is heated to 80° C. At 10 min intervals, samples are taken from the reaction solution, and pH measurements are performed. Already from the first measurement, a fast decrease of the pH value down to pH 1-2 is found. This leads one to conclude that hydrolytic decomposition of the ionic liquid occurs under such reaction conditions to release ethanol and the acidic hydrogensulfate anion.

Characterization Example 3

Viscosity Measurement with the Ionic Liquid (1-butyl-3-methylimidazolium) (C$_9$H$_{17}$—O—SO$_3$)

The following viscosities were determined for (1-butyl-3-methylimidazolium) (C$_8$H$_{17}$—O—SO$_3$):
20° C.; η=874 cP±10 cP
40° C.; η=262 cP±5 cP
60° C.; η=97 cP±3 cP
80° C.; η=46 cP±2 cP

Method of Use Example 1

Rh-Catalyzed Hydroformylation of 1-Octene Using (1-butyl-3-methylimidazolium) (Me(O—CH$_2$—CH$_2$)$_2$—O—SO$_3$) as the Solvent 0.05 mmol of Rh(acac)(CO)$_2$ and 0.10 mmol of the ligand NaTPPTS are added to a Schlenk tube with weighing. 5 ml of the ionic liquid (1-butyl-3-methylimidazolium) (Me(O—CH$_2$—CH$_2$)$_2$—O—SO$_3$) and 5 ml of cyclohexane are added. This two-phase solution is quantitatively transferred into an autoclave which was equipped with a cross-shaped magnetic stirring bar. The autoclave is pressurized with synthesis gas (CO/H$_2$ ratio=1/1, heated at 100° C., and synthesis gas is released in such an amount that the pressure is 30 bar. After a preformation time of 30 min, 50 mmol of 1-octene is added through a dropping funnel with pressure compensation. After a reaction time of 1 h, fast cooling to room temperature is achieved by means of ice cooling, and the synthesis gas pressure is released. The organic phase is analyzed by means of GC; 46.8% of 1-octene is converted. The selectivity towards aldehydes is >95%, which corresponds to a catalyst activity (turnover frequency) of 480 mol of aldehyde per mole of Rh*h. The ratio of the linear aldehydes formed to the branched aldehydes formed is 2.6.

Comparative Method of Use Example 1

Rh-Catalyzed Hydroformylation of 1-octene Using (1-butyl-3-methylimidazolium) ($C_8H_{17}$—O—$SO_3$) as the Solvent 0.05 mmol of Rh(acac)(CO)$_2$ and 0.10 mmol of the ligand NaTPPTS are added to a Schlenk tube with weighing. 5 ml of the ionic liquid (1-butyl-3-methylimidazolium) ($C_8H_{17}$—O—$SO_3$) and 5 ml of cyclohexane are added. This two-phase solution is quantitatively transferred into an autoclave which was equipped with a cross-shaped magnetic stirring bar. The autoclave is pressurized with synthesis gas (CO/H$_2$ ratio=1/1, heated at 100° C., and synthesis gas is released in such an amount that the pressure is 30 bar. After a preformation time of 30 min, 50 mmol of 1-octene is added through a dropping funnel with pressure compensation. After a reaction time of 1 h, fast cooling to room temperature is achieved by means of ice cooling, and the synthesis gas pressure is released. The organic phase is analyzed by means of GC; 15.6% of 1-octene is converted. The selectivity towards aldehydes is >95%, which corresponds to a catalyst activity (turnover frequency) of 160 mol of aldehyde per mole of Rh*h. The ratio of the linear aldehydes formed to the branched aldehydes formed is 2.6.

The disclosures of the references cited herein are hereby incorporated in their entirety.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except by the appended claims. All of the embodiments disclosed and claimed herein can be made and executed without undue experimentation in light of the present disclosure.

The invention claimed is:

1. An ionic liquid comprising a compound with the general formula:

(anion)(cation)        Formula III wherein
  (anion) is independently selected as each occurrence from the group consisting of (R'—O—SO$_3$) and (R'—SO$_3$);
  R' represents a group of general formula $R^5$—(X(—CH$_2$—)$_n$)$_m$ in which n represents a number from 1 to 12;
  m represents a number independent of n of from 1 to 400, from 50 to 300, or from 100 to 200;
  X represents —O—; and
  $R^5$ represents a linear or branched, saturated or unsaturated, aliphatic or alicyclic alkyl group having 1-36 carbon atoms non-functionalized; and
  (cation) is independently selected at each occurrence from the group consisting of:
    imidazolium cation of general formula

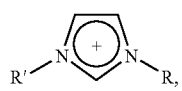

wherein the imidazole nucleus may be substituted with at least one group selected from $C_{1-6}$ alkyl;
    pyridinium cation of general formula

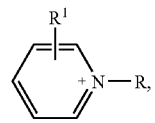

wherein the pyridine nucleus may be substituted with at least one group selected from $C_{1-6}$ alkyl; and
    pyrazolium cation of general formula

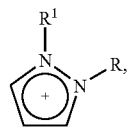

wherein the residues $R^1$ is independently selected at each occurrence from the group consisting of:
      hydrogen; and
      linear or branched, saturated or unsaturated, aliphatic or alicyclic alkyl groups having from 1 to 20 carbon atoms; and
    the residue R is selected from
      linear or branched, saturated or unsaturated, aliphatic or alicyclic alkyl groups having 1 to 20, 5 to 15, or 8 to 12 carbon atoms when (cation) is imidazolium cation or pyrazolium cation, or linear or branched, saturated or unsaturated, aliphatic or alicyclic alkyl groups having 1 to 15, 5 to 15 or 8 to 12 carbon atoms when (cation) is pyridinium cation.

2. The ionic liquid according to claim 1, characterized in that said ionic liquid comprises an anion of formula (Me(O—CH$_2$—CH$_2$)$_n$—O—SO$_3$), wherein n is a number of from 1 to 12.

3. The ionic liquid according to claim 2, characterized in that n is selected from 3, 4 or 5.

4. The ionic liquid according to claim 1, characterized in that said ionic liquid comprises an anion of formula (Me(O—CH$_2$—CH$_2$)$_n$—SO$_3$), wherein n is a number of from 1 to 12.

5. The ionic liquid according to claim 1, characterized in that n is selected from 2 or 3.

6. The ionic liquid of claim 1, wherein the ionic liquid is selected from the group consisting of:
  (1-ethyl-3-methylimidazolium) (Me(O—CH$_2$—CH$_2$)$_2$—O—SO$_3$)
  (1-ethyl-3-methylimidazolium) (Me(O—CH$_2$—CH$_2$)$_3$—O—SO$_3$)
  (1-ethyl-3-methylimidazolium) (Me(O—CH$_2$—CH$_2$)$_4$—O—SO$_3$)
  (1-ethyl-3-methylimidazolium) (Me(O—CH$_2$—CH$_2$)$_5$—O—SO$_3$)
  (1-ethyl-3-methylimidazolium) (Me(O—CH$_2$—CH$_2$)$_2$—SO$_3$)
  (1-ethyl-3-methylimidazolium) (Me(O—CH$_2$—CH$_2$)$_3$—SO$_3$)
  (1-butyl-3-methylimidazolium) (Me(O—CH$_2$—CH$_2$)$_2$—O—SO$_3$)
  (1-butyl-3-methylimidazolium) (Me(O—CH$_2$—CH$_2$)$_3$—O—SO$_3$)
  (1-butyl-3-methylimidazolium) (Me(O—CH$_2$—CH$_2$)$_4$—O—SO$_3$)

(1-butyl-3-methylimidazolium) (Me(O—CH$_2$—CH$_2$)$_5$—O—SO$_3$)
(1-butyl-3-methylimidazolium) (Me(O—CH$_2$—CH$_2$)$_2$—SO$_3$)
(1-butyl-3-methylimidazolium) (Me(O—CH$_2$—CH$_2$)$_3$—SO$_3$)
(1-octyl-3-methylimidazolium) (Me(O—CH$_2$—CH$_2$)$_2$—O—SO$_3$)
(1-octyl-3-methylimidazolium) (Me(O—CH$_2$—CH$_2$)$_3$—O—SO$_3$)
(1-octyl-3-methylimidazolium) (Me(O—CH$_2$—CH$_2$)$_4$—O—SO$_3$)
(1-octyl-3-methylimidazolium) (Me(O—CH$_2$—CH$_2$)$_5$—O—SO$_3$)
(1-octyl-3-methylimidazolium) (Me(O—CH$_2$—CH$_2$)$_2$—SO$_3$)
(1-octyl-3-methylimidazolium) (Me(O—CH$_2$—CH$_2$)$_3$—SO$_3$)
(1-dodecyl-3-methylimidazolium) (Me(O—CH$_2$—CH$_2$)$_2$—O—SO$_3$)
(1-dodecyl-3-methylimidazolium) (Me(O—CH$_2$—CH$_2$)$_3$—O—SO$_3$)
(1-dodecyl-3-methylimidazolium) (Me(O—CH$_2$—CH$_2$)$_4$—O—SO$_3$)
(1-dodecyl-3-methylimidazolium) (Me(O—CH$_2$—CH$_2$)$_5$—O—SO$_3$)
(1-dodecyl-3-methylimidazolium) (Me(O—CH$_2$—CH$_2$)$_2$—SO$_3$)
(1-dodecyl-3-methylimidazolium) (Me(O—CH$_2$—CH$_2$)$_3$—SO$_3$)
(1-methylimidazolium) (Me(O—CH$_2$—CH$_2$)$_2$—O—SO$_3$)
(1-methylimidazolium) (Me(O—CH$_2$—CH$_2$)$_3$—O—SO$_3$)
(1-methylimidazolium) (Me(O—CH$_2$—CH$_2$)$_4$—O—SO$_3$)
(1-methylimidazolium) (Me(O—CH$_2$—CH$_2$)$_5$—O—SO$_3$)
(1-methylimidazolium) (Me(O—CH$_2$—CH$_2$)$_2$—SO$_3$)
(1-methylimidazolium) (Me(O—CH$_2$—CH$_2$)$_3$—SO$_3$)
(1-butylpyridinium) (Me(O—CH$_2$—CH$_2$)$_2$—O—SO$_3$)
(1-butylpyridinium) (Me(O—CH$_2$—CH$_2$)$_3$—O—SO$_3$)
(1-butylpyridinium) (Me(O—CH$_2$—CH$_2$)$_4$—O—SO$_3$)
(1-butylpyridinium) (Me(O—CH$_2$—CH$_2$)$_5$—O—SO$_3$)
(1-butylpyridinium) (Me(O—CH$_2$—CH$_2$)$_2$—SO$_3$) and
(1-butylpyridinium) (Me(O—CH$_2$—CH$_2$)$_3$—SO$_3$).

7. The ionic liquid of claim 1, wherein the ionic liquid has a melting point or glass point of 25° C. or lower.

8. The ionic liquid of claim 1 or 7, wherein the ionic liquid has a viscosity of 0.8 Pa·s at 20° C. (800 cPs at 20° C.) or lower.

9. An ionic liquid comprising cation and anion, wherein the cation is selected from the group consisting of (1-ethyl-3-methylimidazolium), (1-butyl-3-methylimidazolium), (1-methylimidazolium), (1-octyl-3-methylimidazolium), (1-dodecyl-3-methylimidazolium), (1-butylpyridinium), and (pyridinium), and the anion is selected from the group consisting of (Me(O—CH$_2$—CH$_2$)$_2$—O—SO$_3$), (Me(O—CH$_2$—CH$_2$)$_3$—O—SO$_3$), (Me(O—CH$_2$—CH$_2$)$_4$—O—SO$_3$), (Me(O—CH$_2$—CH$_2$)$_5$—O—SO$_3$), (Me(O—CH$_2$—CH$_2$)$_2$—SO$_3$), and (Me(O—CH$_2$—CH$_2$)$_3$—SO$_3$).

10. The ionic liquid of claim 1, wherein (anion) is the same at each occurrence.

11. The ionic liquid of claim 1, wherein (anion) is a mixture of two or more different (anion).

12. The ionic liquid of claim 1, wherein (cation) is the same at each occurrence.

13. The ionic liquid of claim 1, wherein (cation) is a mixture of two or more different (cation).

14. The ionic liquid of claim 1, wherein the ionic liquid is a mixture or two or more different ionic liquids.

15. The ionic liquid of claim 1, wherein the ionic liquid is selected from the group consisting of:

(1-ethyl-3-methylimidazolium) (Et(O—CH$_2$—CH$_2$)$_2$—O—SO$_3$)
(1-ethyl-3-methylimidazolium) (Et(O—CH$_2$—CH$_2$)$_3$—O—SO$_3$)
(1-ethyl-3-methylimidazolium) (Et(O—CH$_2$—CH$_2$)$_4$—O—SO$_3$)
(1-ethyl-3-methylimidazolium) (Et(O—CH$_2$—CH$_2$)$_5$—O—SO$_3$)
(1-ethyl-3-methylimidazolium) (Et(O—CH$_2$—CH$_2$)$_2$—SO$_3$)
(1-ethyl-3-methylimidazolium) (Et(O—CH$_2$—CH$_2$)$_3$—SO$_3$)
(1-butyl-3-methylimidazolium) (Et(O—CH$_2$—CH$_2$)$_2$—O—SO$_3$)
(1-butyl-3-methylimidazolium) (Et(O—CH$_2$—CH$_2$)$_3$—O—SO$_3$)
(1-butyl-3-methylimidazolium) (Et(O—CH$_2$—CH$_2$)$_4$—O—SO$_3$)
(1-butyl-3-methylimidazolium) (Et(O—CH$_2$—CH$_2$)$_5$—O—SO$_3$)
(1-butyl-3-methylimidazolium) (Et(O—CH$_2$—CH$_2$)$_2$—SO$_3$)
(1-butyl-3-methylimidazolium) (Et(O—CH$_2$—CH$_2$)$_3$—SO$_3$)
(1-octyl-3-methylimidazolium) (Et(O—CH$_2$—CH$_2$)$_2$—O—SO$_3$)
(1-octyl-3-methylimidazolium) (Et(O—CH$_2$—CH$_2$)$_3$—O—SO$_3$)
(1-octyl-3-methylimidazolium) (Et(O—CH$_2$—CH$_2$)$_4$—O—SO$_3$)
(1-octyl-3-methylimidazolium) (Et(O—CH$_2$—CH$_2$)$_5$—O—SO$_3$)
(1-octyl-3-methylimidazolium) (Et(O—CH$_2$—CH$_2$)$_2$—SO$_3$)
(1-octyl-3-methylimidazolium) (Et(O—CH$_2$—CH$_2$)$_3$—SO$_3$)
(1-dodecyl-3-methylimidazolium) (Et(O—CH$_2$—CH$_2$)$_2$—O—SO$_3$)
(1-dodecyl-3-methylimidazolium) (Et(O—CH$_2$—CH$_2$)$_3$—O—SO$_3$)
(1-dodecyl-3-methylimidazolium) (Et(O—CH$_2$—CH$_2$)$_4$—O—SO$_3$)
(1-dodecyl-3-methylimidazolium) (Et(O—CH$_2$—CH$_2$)$_5$—O—SO$_3$)
(1-dodecyl-3-methylimidazolium) (Et(O—CH$_2$—CH$_2$)$_2$—SO$_3$)
(1-dodecyl-3-methylimidazolium) (Et(O—CH$_2$—CH$_2$)$_3$—SO$_3$)
(1-methylimidazolium) (Et(O—CH$_2$—CH$_2$)$_2$—O—SO$_3$)
(1-methylimidazolium) (Et(O—CH$_2$—CH$_2$)$_3$—O—SO$_3$)
(1-methylimidazolium) (Et(O—CH$_2$—CH$_2$)$_4$—O—SO$_3$)
(1-methylimidazolium) (Et(O—CH$_2$—CH$_2$)$_5$—O—SO$_3$)
(1-methylimidazolium) (Et(O—CH$_2$—CH$_2$)$_2$—SO$_3$)
(1-methylimidazolium) (Et(O—CH$_2$—CH$_2$)$_3$—SO$_3$)
(1-butylpyridinium) (Et(O—CH$_2$—CH$_2$)$_2$—O—SO$_3$)
(1-butylpyridinium) (Et(O—CH$_2$—CH$_2$)$_3$—O—SO$_3$)
(1-butylpyridinium) (Et(O—CH$_2$—CH$_2$)$_4$—O—SO$_3$)
(1-butylpyridinium) (Et(O—CH$_2$—CH$_2$)$_5$—O—SO$_3$)
(1-butylpyridinium) (Et(O—CH$_2$—CH$_2$)$_2$—SO$_3$) and
(1-butylpyridinium) (Et(O—CH$_2$—CH$_2$)$_3$—SO$_3$).

16. The ionic liquid of claim 1, wherein the cation is selected from the group consisting of (1,3-dimethylimidazolium), (1-ethyl-3-methylimidazolium), (1-propyl-3-methylimidazolium), (1-ethyl-2,3-dimethylimidazolium), (1-butyl-2,3-dimethylimidazolium), (1,2-dimethyl-3-octylimidazolium), (1-butyl-3-methylimidazolium), (1-methylimidazolium), (1-ethylimidazolium), (1-butylimidazolium), (1-octylimidazolium), (1-hexyl-3-methylimidazolium), (1-octyl-3-methylimidazolium), (1-dodecyl-3-methylimidazolium), (1-methylpyridinium), (1-ethylpyridinium), (1-butylpyridinium), and (pyridinium) and the anion is selected from the group consisting of (Et(O—CH$_2$—CH$_2$)$_2$—O—SO$_3$), (Et(O—CH$_2$—CH$_2$)$_3$—O—SO$_3$), (Et(O—CH$_2$—CH$_2$)$_4$—O—SO$_3$), (Et(O—CH$_2$—CH$_2$)$_5$—O—SO$_3$), (Et(O—CH$_2$—CH$_2$)$_2$—SO$_3$), (Et(O—CH$_2$—CH$_2$)$_3$—SO$_3$), (Bu(O—CH$_2$—CH$_2$)$_2$—O—SO$_3$), (Bu(O—CH$_2$—CH$_2$)$_3$—O—SO$_3$), (Bu(O—CH$_2$—CH$_2$)$_4$—O—SO$_3$), (Bu(O—CH$_2$—CH$_2$)$_5$—O—SO$_3$), (Bu(O—CH$_2$—CH$_2$)$_2$—SO$_3$), (Bu(O—CH$_2$—CH$_2$)$_3$—SO$_3$), (Et(S—CH$_2$—CH$_2$)$_2$—O—SO$_3$), and (Et(O—Si(CH$_3$)$_2$—O—CH$_2$—CH$_2$)$_2$—O—SO$_3$).

17. The ionic liquid of claim 1, wherein the cation is selected from the group consisting of (1,3-dimethylimidazolium), (1-propyl-3-methylimidazolium), (1-ethyl-2,3-dimethylimidazolium), (1-butyl-2,3-dimethylimidazolium), (1,2-dimethyl-3-octylimidazolium), (1-ethylimidazolium), (1-butylimidazolium), (1-octylimidazolium), (1-hexyl-3-methylimidazolium), (1-methylpyridinium), and (1-ethylpyridinium), and the anion is selected from the group consisting of (Me(O—CH$_2$—CH$_2$)$_2$—O—SO$_3$), (Me(O—CH$_2$—CH$_2$)$_3$—O—SO$_3$), (Me(O—CH$_2$—CH$_2$)$_4$—O—SO$_3$), (Me(O—CH$_2$—CH$_2$)$_5$—O—SO$_3$), (Me(O—CH$_2$—CH$_2$)$_2$—SO$_3$), and (Me(O—CH$_2$—CH$_2$)$_3$—SO$_3$).

\* \* \* \* \*